(12) United States Patent
Lavallée (10) Patent No.: US 7,618,419 B2
(45) Date of Patent: Nov. 17, 2009

(54) METHOD AND SYSTEM OF COMPUTER ASSISTANCE FOR THE REDUCTION OF A FRACTURE

(75) Inventor: Stéphane Lavallée, Saint Martin d'Uriage (FR)

(73) Assignee: Universite Joseph Fourier, Grenoble (FR)

( * ) Notice: Subject to any disclaimer, the term of this patent is extended or adjusted under 35 U.S.C. 154(b) by 458 days.

(21) Appl. No.: 11/334,944

(22) Filed: Jan. 18, 2006

(65) Prior Publication Data
US 2006/0241388 A1 Oct. 26, 2006

(30) Foreign Application Priority Data
Jan. 18, 2005 (FR) .................... 05 50148

(51) Int. Cl.
*A61B 17/64* (2006.01)
*A61B 8/00* (2006.01)
(52) U.S. Cl. ..................... 606/86 R; 600/437
(58) Field of Classification Search ............. 600/407, 600/416, 429, 427, 300, 437–440; 606/86 R, 606/50–72, 102
See application file for complete search history.

(56) References Cited
U.S. PATENT DOCUMENTS
2003/0004518 A1 1/2003 Perren et al.
2004/0019263 A1* 1/2004 Jutras et al. .................. 600/407

FOREIGN PATENT DOCUMENTS
FR 2798760 A 3/2001
JP 2003339725 A 12/2003

OTHER PUBLICATIONS

Ofer, Ron et al., Computer-Based Periaxial Rotation Measurement for Aligning Fractured Femur Fragments from CT: A Feasibility Study, Computer Aided Surgery 7:332-341 (2002).
International Search Report FR 0550148.

* cited by examiner

*Primary Examiner*—Eric F Winakur
*Assistant Examiner*—Lawrence N Laryea
(74) *Attorney, Agent, or Firm*—Leason Ellis LLP (57) ABSTRACT

A method and system of computer assistance to the preparation of the reduction of a fracture such that a patient's bony fragments are separated into first and second bone segments, with in bone segments being symmetrical to a third bone element. The method includes the steps of determining a first representation or bone model of the surface of the first bone segment, a second representation, at an initial position, of the second segment, and a third representation of the third bone element; determining by symmetry a fourth representation of the first and second bone segments of the fractured bone in the absence of a fracture, the fourth representation being matched with the first representation; matching the second representation with the fourth representation at a final position; and providing, by an interface element, information representative of the difference between the initial position and the final position.

19 Claims, 3 Drawing Sheets

METHOD AND SYSTEM OF COMPUTER ASSISTANCE FOR THE REDUCTION OF A FRACTURE

CROSS REFERENCE TO RELATED APPLICATIONS

The present application claims priority to French Patent Application No. 05/50148 filed Jan. 18, 2005, the disclosure of which is incorporated herein by reference.

BACKGROUND

1. Technical Field

The present invention relates to the repair of bone fractures, in particular, the present invention relates to a method and system for the computer assisted repair of bone fractures.

2. Discussion of the Related Art

Generally, in repairing bone fractures, the bone must be reduced. Reduction is a medical procedure to restore a fracture or dislocation to the correct alignment. When a bone fractures, the fragments lose their alignment in the form of displacement or angulation. For the fractured bone to heal without any deformity the bony fragments must be re-aligned to their normal anatomical position. This repositioning step is generally the most difficult, since it is difficult for the surgeon or physician to appreciate how to precisely orient the portions of the fractured bone. For example, in the case of a long bone single fracture, two bony fragments are generated and are generally repaired with a nail (or external plate or pin), that for example may enter the medullar cavity of the bone. The nail (or plate) is then attached to the distal and proximal ends of the bone by screws. In the specific case of the femur, the nail is typically introduced into the medullar cavity through the proximal end and then attached to the distal end.

A conventional method for assisting surgeons before and during the reduction of a fracture includes the use of two-dimensional images such as fluoroscopy image data. Based upon the fluoroscopy data, the surgeon can perform the necessary reduction to reposition the bony fragments or elements. Once the bony fragments have been properly positioned and nailed, additional fluoroscopy images are obtained to facilitate placement of nail attachment screws.

The article entitled: "FRACAS: A System for Computer-Aided Image-Guided Long Bone Fracture Surgery" by Joskowicz et al., Comp. Aid Surg. 1999; 3(6):271-288, describes a computer-assisted method for the reduction of a fracture for a long bone that includes the steps of; forming a three-dimensional model, for example, by tomography data, of the external surface of a healthy bone, for example a femur bone, to assist the surgeon in the selection of the length and of the diameter of the nail to be used to connect the portions of the fractured bone, forming three-dimensional models, also by tomography data, of the external surfs of the proximal and distal portions of the fractured bone, tracking the positions of the proximal and distal portions with a three-dimensional positioning system, readjusting the models of the proximal and distal portions in accordance with the positions of the proximal and distal portions of the fractured bone obtained by fluoroscopy, tracking in real time on a screen images representative of the proximal and distal portions manipulated by the surgeon to assist him in the repositioning of the proximal and distal portions; and forming a new set of two-dimensional images by fluoroscopy to check the relative positions between the proximal and distal portions to insert an attachment nail.

The method described in article "FRACAS" has the advantage of decreasing the number of images to be acquired by fluoroscopy since the tracking of the displacements of the osseous portions is performed based on previously-determined three-dimensional models. However, such as method requires a pre-operative study to form the three-dimensional models by tomography. Further, the acquisition of images by radiation based imaging (i.e., fluoroscopy) is not completely eliminated.

BRIEF SUMMARY OF THE INVENTION

The present invention provides for a fracture-reduction assistance method and system that provides the surgeon with information as to the necessary bone manipulations or repositioning necessary to perform a reduction of the fractured bone.

Another object of the present invention is to provide a fracture-reduction assistance method and system without the uses of irradiation based imaging techniques. To achieve these objects, the present invention provides a method of computer assistance for the preparation of the reduction of a fracture. The method includes the steps of: (a) determining a first three-dimensional image representative of the surface of the first osseous portion of the fractured osseous element, a second three-dimensional image, at an initial position, representative of the surface of the second osseous portion of the fractured osseous element, and a third three-dimensional image representative of the surface of the regions of the additional osseous element corresponding to the first and second portions of the fractured osseous element; (b) determining by symmetry, based on the third three-dimensional image, a fourth three-dimensional image representative of the surface of the first and second portions of the fractured osseous element in the absence of a fracture, the fourth three-dimensional image being matched with the first three-dimensional image; (c) matching the second three-dimensional image with the fourth three-dimensional image at a final position; and (d) providing, by an interface element, information representative of the difference between the initial position and the final position.

According to one embodiment, the step of determining the fourth three-dimensional image includes the steps of determining by symmetry, based on the third three-dimensional image, a theoretical three-dimensional image representative of the surface of the first and second bone segments of the fractured bone in the absence of a fracture; and of matching the theoretical three-dimensional image with the first three-dimensional image.

According to one embodiment, at least one of the first, second, and third three-dimensional images is determined based on at least one image obtained by ultrasound scanning.

According to one embodiment, at least one of the first, second, and third three-dimensional images is determined based on two-dimensional images obtained by ultrasound scanning.

According to one embodiment, the step of determining the first three-dimensional image and/or the second three-dimensional image includes the steps of determining characteristic points of the first osseous portion and/or of the second osseous portion; and deforming a model of the first osseous portion and/or a model of the second osseous portion to have it match the points.

According to one embodiment, the step of determining the third three-dimensional image includes the steps of determining characteristic points of the additional osseous element; and deforming a model of the additional osseous element to have it correspond to the points.

The present invention also provides a computer assisted system for the preparation of the reduction of a fracture. The system includes a first three-dimensional image or bone model representative of the first bone segment portion of the fractured bone. The system further includes a second three-dimensional image, at an initial position, representative of the second bone segment of the fractured bone or osseous element. The system further includes a third three-dimensional image representative of the regions of the additional osseous element corresponding to the first and second portions of the fractured osseous element. The system further includes a computer for determining by symmetry, based on the third three-dimensional image. The system further includes a fourth three-dimensional image representative of the first and second portions of the fractured osseous element in the absence of a fracture with the fourth three-dimensional image being matched with the first three-dimensional image; as well as matching the second three-dimensional image with the fourth three-dimensional image at a final position. The system further includes an interface element; and provides, by the interface element, information representative of the difference between the initial position and the final position.

According to one embodiment, the first, second, and third three-dimensional images is formed from images produced by an ultrasound probe.

According to one embodiment, the system further includes a tridimensional positioning system for determining the position of each portion of the fractured osseous element with respect to a reference system.

According to one embodiment, the interface includes a display screen and, the device further includes a display screen for displaying at least one image or bone model representative of each portion of the fractured osseous element or bone segment based on the position of each portion of the fractured osseous element or fractured bone.

DETAILED DESCRIPTION OF THE INVENTION

As used herein, the following definitional terms apply. "Anterior" and "posterior" mean nearer to the front or the back of the body respectively. "Proximal" and "distal" mean nearer and farther from the center of the body respectively. "Medial" and "lateral" mean nearer or farther from the median plane respectively. The median plane is an imaginary, vertical plane that divides the body into a right and left half. The coronal plane is an imaginary, vertical plane that divides the body into a front half and a back half. "Superior" and "inferior" mean above or below respectively. For example, the distal femur has medial and lateral condyles that are superior to the proximal tibia. "Sagittal" means a side profile. Varus means turned inward and valgus means turned outward or away from the body.

The present invention is based on the property that almost all the bones of the body are symmetric about the median plane. "Symmetrical bone" is used to designate a bone such that a individual includes two samples symmetrical to each other of said bone, or a bone having portions that can be considered as symmetrical to each other. Examples of the first category are long bones such as the femur, the tibia, the fibula, the radius, the cubitus, the ribs, the metacarpus or metatarsus bones, etc., or bones, which are not long bones, such as shoulder blades, the carpus or tarsus bones. Examples of the second category are bones which are located in the median plane of vertebrates such as the skull, the pelvis, each vertebra, etc. The property of symmetry of bones enables one to reposition bony fragments based on bony landmarks or characteristics of the bone and its symmetrical bony element or counterpart. The present invention will be described in the context of the reduction of a fracture of the femur, however knowing that it may apply to any symmetrical bone reduction, from as soon as it is necessary to reposition bony fragments of the fractured bone with respect to each other before connecting them. According to the present invention, certain characteristics of a patient's healthy, that is, non-fractured, femur are used to assist the surgeon in the reduction of the patient's fractured femur.

In the case of the femur, and more generally of a long bone, a fracture reduction is generally necessary when the fracture occurs at the level of the diaphysis, separating the bone into two portions called the first bone segment (i.e., a proximal portion) and the second bone segment (i.e., a distal portions). A third bone element is called the symmetrical bone (in the present example, if the right femur is the fractured bone, then the third bone element would be the left femur).

Figure 1:
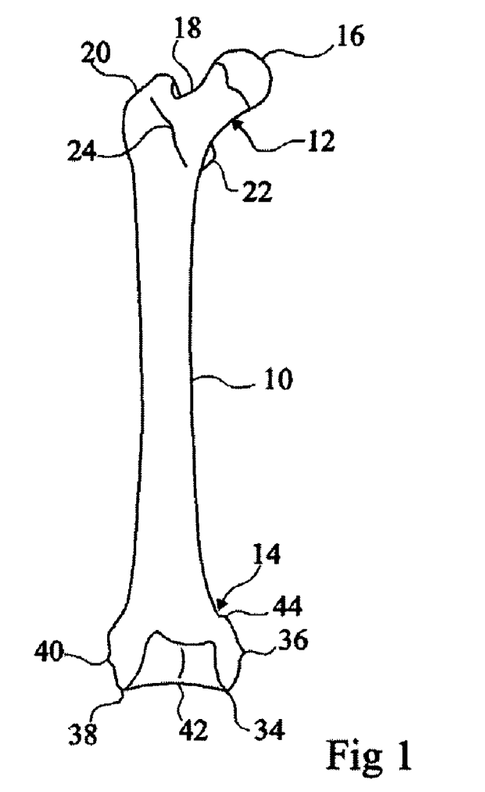
FIG. 1 is an anterior view of a femur.
Figure 2:
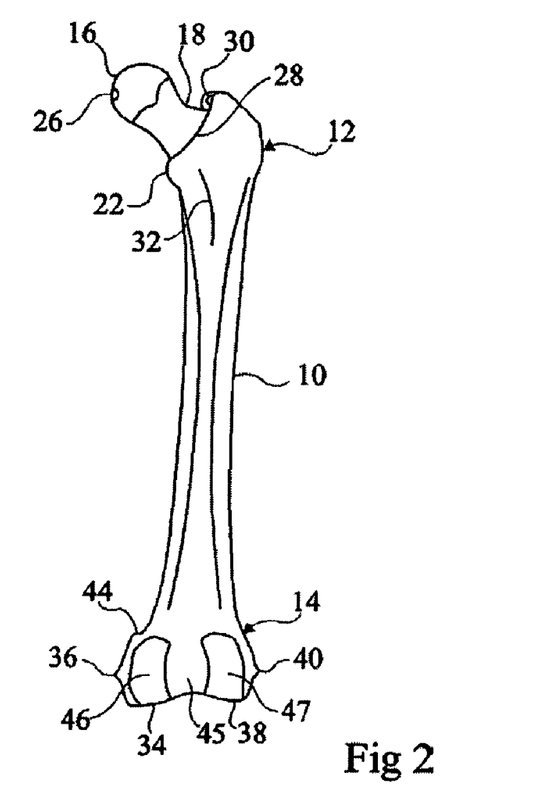
FIG. 2 is a posterior view of the femur of FIG. 1.

FIGS. 1 and 2 respectively show an anterior and posterior view of a healthy femur bone 10 having a proximal end 12 and a distal end 14.

The present invention first includes the defining of a three-dimensional image or bone model representative of the surface of femur 10. According to a variation, two three-dimensional images respectively representative of the surface of proximal end 12 and of the surface of distal end 14 of healthy femur 10 are determined. In this last case, the relative position between the two three-dimensional images is memorized.

According to an example of an embodiment of the method according to the present invention, the three-dimensional image of the surface of the patient's healthy femur 10 is determined based on two-dimensional images of femur 10 obtained by ultrasound scanning intra-operatively. The two-dimensional images can also be obtained based upon any other non-radiation based imaging devices known in the art. The three-dimensional image may be automatically generated with a computer based on the two-dimensional images by extracting the contour of femur 10 on the two-dimensional images. The determination of the femur contour on images obtained by an ultrasound probe may be performed according to the techniques described in the following documents:

"A Fully Automated Method for the Delineation of Osseous Interface in Ultrasound Images" by Vincent Daanen, Jérôme Tonetti, and Jocelyne Troccaz (MICCAI (1) 2004: 549-557);

"Automatic Delineation of Osseous Interface in Ultrasound Images by Data Fusion" by Vincent Daanen, Jérôme Tonetti, and Jocelyne Troccaz (CARS 2004: 1245);

"Ultrasound Registration of the Bone Surface for Surgical Navigation" by D. Amin, T. Kanade, A. M. DiGioia III, and B. Jamaraz (Computer Aided Surgery Vol. 8, No. 1, January, 2003, pp. 1-16); and "Computer Understanding Bone Responses in B-Mode Ultrasound Images and Automatic Bone Sure Extraction Using a Bayesian Probabilistic Framework" by Ammet K. Jain and Russel H. Taylor, Medical Imaging 2004: Ultrasonic Imaging and Signal Processing published by Walker, William F.; Emelianov, Stanislav Y. Proceedings of the SPIE, Volume 5373, pp. 131-142 (2004). (Which are all hereby incorporated by reference in their entirety).

According to an example of embodiment of the method according to the present invention, the position of the ultrasound probe is determined by a tridimensional positioning system or localization system (not shown). From the position of the ultrasound probe, it is then possible to acquire the position of the planes of the images provided by the ultrasound probe. The determination of the position of images obtained by an ultrasound probe can be performed according to the techniques described in the following documents:

"Calibration method for determining the physical location of the ultrasound image plane" by Amin D V, Kanade T, DiGioia A M, Jaramaz B, Nikou C, LaBarca R S, Moody J E. Proceedings of the Fourth International Conference of Medical Image Computing and Computer-Assisted Intervention (MICCAI 2001), Utrecht, The Netherlands, October, 2001

According to a variation, a three-dimensional model of the surface of healthy femur 10 may be used and modified according to the two-dimensional images obtained by ultrasound scanning. An example of a method for deforming a three-dimensional model of the surface of a bone is described in documents "Incorporating a Statistically Based Shape Model into a System for Computer-Assisted Anterior Cruciate Ligament Surgery" by M. Fleute, S. Lavallee, R. Julliard (Medical Image Analysis. 1999 September, 3(3): 209-222) and U.S. Patent Application Publication No. 2005/0101966A1, published May 12, 2005. (The above cited documents being incorporated by reference in their entirety). As an example, the contour of femur 10 is determined for each two-dimensional image and the three-dimensional model of the femur is deformed to have it match the contours thus extracted from the two-dimensional images. Such an operation may be automatically performed by a computer. The three-dimensional model may be used to help the identification of the contour of femur 10 on the two-dimensional images, taking the three-dimensional model as a staring point for the search for the femur contour on the two-dimensional images.

According to a variation, instead of adapting the three-dimensional model to the bone contours determined based on the two-dimensional images obtained by ultrasound scanning, the three-dimensional model is deformed to have it match characteristic anatomic points determined based on the two-dimensional images. According to another variation, characteristic anatomic points may be used to, in an initial step, correctly orient the three-dimensional model and perform an enlargement or a reduction of the three-dimensional model to scale it properly. The three-dimensional model is then deformed to match with contours, with characteristic points, or with characteristic points and contours. Characteristic points of the surface of bone 10 adapted to the determination of the three-dimensional image of bone 10 are shown in FIGS. 1 and 2. Examples of remarkable characteristic points at the level of proximal end 12 include but are not limited to: the endmost point of the apophysis of femur 16; the most proximal point of the neck of femur 18; the midpoint of great trochanter 20; the end point of lesser trochanter 22; the midpoint of intertrochanteric line 24; the central point of fovea capitis 26; the midpoint of intertrochanteric crest 28; the midpoint of trochanteric fossa 30; and the midpoint of the crest of pectin 32. Examples of remarkable characteristic points at the level of distal end 14 include but are not limited to: the most distal point of medial condyle 34; the end point of medial epicondyle 36; the most distal point of lateral condyle 38; the end point of lateral epicondyle 40; the most distal point of femoral trochlea 42; the end point of the tubercle of adductor 44; and the midpoint of intercondylar fossa 45; the point of the medial condyle in contact with a plane on which femur 10 would be laid on posterior side 46; and the point of the lateral condyle in contact with a plane on which femur 10 would be laid on posterior side 47.

More specifically, the method for determining the characteristic points of the surface of bone 10 based on two-dimensional images obtained by ultrasound scanning can be an automated process including a computer analysis of each image based on predefined criteria. Such criteria correspond, for example, to specific geometric characteristics associated with the characteristic points. As an example, for each image, the computer automatically determines the bone contour according to the predefined criteria. For example, for the end point of medial epicondyle 36 and the end points of lateral epicondyle 40, the computer can search the contour points for which the tangent to the contour abruptly varies.

The method for determining the characteristic points can also be a semi-automated process, in which the two-dimensional image provided by the ultrasound probe is permanently displayed on a screen or display and updated as the surgeon moves the probe with respect to the patient. More specifically, the image provided by the ultrasound scan probe is displayed to show the probe axis as an axis of reference, for example, vertical, on the screen, superposed to the image provided by the ultrasound scan probe. The surgeon can then displace the ultrasound scan probe until the axis of reference cuts the ultrasound image at the level of a region which, for the surgeon, corresponds to a characteristic anatomic point. The surgeon then indicates to the computer that the axis of reference is at the level of the characteristic point, and the computer can then refine the search for the characteristic point around the position indicated by the axis of reference.

According to a variation of the present invention, the three-dimensional model is obtained by palpation of femur 10 by a palpation tool or device (not shown), the position of which can be determined by a localization system. The palpation tool then enables determining the position of characteristic anatomic points of femur 10. The determination of the three-dimensional image of femur 10 is then obtained by deforming a three-dimensional model of femur 10 to adapt it to the anatomic points determined by palpation.

According to another variation, a three-dimensional image of femur 10 is obtained by combining an analysis of two-dimensional images of femur 10, for example obtained by ultrasound scanning, and the palpation of femur 10. The characteristic anatomic points determined by palpation and the bone contours extracted from the two-dimensional images are then both used to deform the three-dimensional model of bone 10 and obtain a three-dimensional image of the bone.

Figure 3:
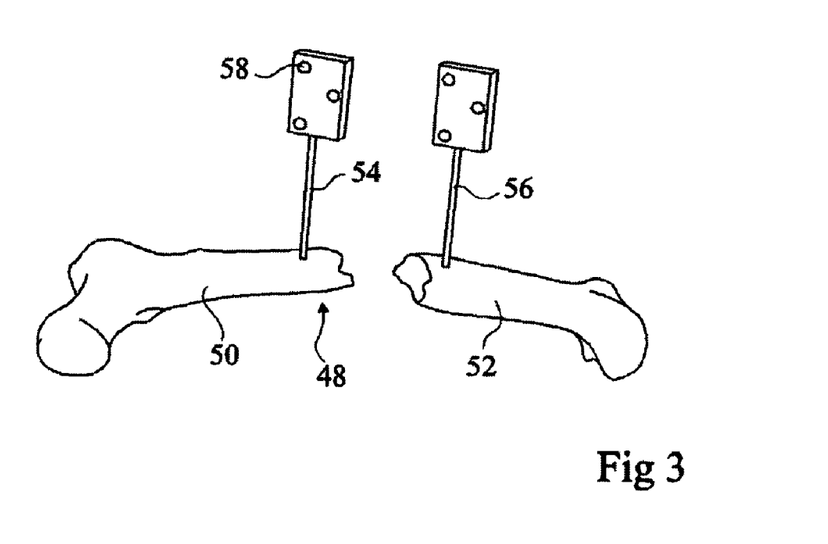
FIG. 3 is a perspective view of the femur of FIG. 1 with a fracture along the diaphysis.

FIG. 3 shows a fractured femur 48 divided into a proximal portion 50 and a distal portion 52. The fracture causes a displacement of distal portion 52 with respect to a theoretical portion that it must normally occupy.

A three-dimensional image associated with proximal portion 50 of fractured bone 48 and a three-dimensional image associated with distal portion 52 of fractured bone 48 are determined for fractured bone 48. The three-dimensional images are determined, as explained previously, by the analysis of ultrasound images or based on the palpation of fractured bone 48 or by a combination of the two techniques. Further, a matrix M representative of the relative position of the three-dimensional image associated with proximal portion 50 and the three-dimensional image associated with distal portion 52 is determined. As an example, this matrix may be in the form of what is commonly known as a transformation matrix, having 4 rows and 4 columns, where the nine elements in the first three rows and first three columns represent the rotation matrix, and the three elements in the first three rows and fourth column resent the displacement vector.

Generally, the fracture reduction requires displacing distal portion 52, proximal portion 50 already being in a convenient position. The surgeon may however have to displace proximal portion 50 of fractured bone 48 to a convenient position. The three-dimensional images associated with the proximal and distal portions and matrix M are then preferably determined after displacement of proximal portion 50.

By using the property of symmetry of the patient's femur bones, a three-dimensional image of fractured femur 48, called hereafter a symmetrical image, which would correspond to the three-dimensional image which would be obtained for femur 48 in the absence of a fracture, can be determined based on the three-dimensional image of healthy femur 10. As an example, the three-dimensional image representative of the surface of femur 10 may correspond to a set of points in the space, the coordinates of each point being defined with respect to a reference frame having an axis extending more or less perpendicularly to the patient's median plane. In this case, the symmetrical image is obtained by taking, for each point in the three-dimensional image representative of the surface of femur 10, the point having the opposite coordinate along said axis.

The portion of the symmetrical image corresponding to the proximal portion is then matched with the three-dimensional image of proximal portion 50. Such a surface matching step can be automatically performed by computer by implementing an ICP-type algorithm (Iterative Closest Point). The implementation of such an algorithm is, for example, described in document "A Method for Registration of 3D Shapes" by P. Besl and N. McKay (IEEE Transactions on Pattern Analysis and Machine Intelligence 14(2): 239-256, 1992). (Which is hereby incorporated by reference in its entirety). Once the symmetrical image is matched with the three-dimensional image of proximal portion 50 of fractured femur 48, the three-dimensional image of distal portion 52 is displaced with respect to the three-dimensional image of proximal portion 50 of fractured femur 48 until it is matched with the portion of the symmetrical image corresponding to the distal portion. For each displacement of distal portion 52 of the fractured bone, a matrix M' representative of the relative position between the three-dimensional images of the proximal and distal portions is calculated. When the three-dimensional image of distal portion 52 is matched with the symmetrical image, the value of matrix M' is representative of the desired relative position between proximal and distal portions 50 and 52 after reduction of the fracture.

Based on matrixes M and M', a matrix M" representative of the shift between the position really taken up by distal portion 52, before reduction, and the theoretical position that distal portion 52 should occupy, after reduction can be determined. The computer can display data representative of matrix M" in the form of one or several translation vectors and of one or several rotation angles.

In the case where the patient is perfectly still, the three-dimensional image determination may be performed based on the mere palpation of characteristic points of fractured bone 48 or on the analysis of images obtained by an ultrasound probe. In this case, the determination of matrix M" may be obtained with as little interventions as possible on the patient. In particular, in the case where the three-dimensional images are obtained from the analysis of images obtained by an ultrasound probe, matrix M", representative of the shift between the position really taken up by distal portion 52, before reduction, and the theoretical position that should be occupied by distal portion 52, after reduction, can be obtained without performing incisions on the patient.

To assist the surgeon in the actual reduction of fractured bone 48, a rigid body 54 is attached to proximal portion 50 and a rigid body 56 is attached to distal portion 52. Each rigid body 54, 56 includes retro-reflective markers 58 capable of reflecting infrared radiations. A localization system (not shown), comprising one or several emitters of infrared rays and several infrared ray sensors, is capable of determining the positions of rigid bodies 54, 56 from the infrared signals reflected by markets 58. As a variation, the rigid bodies may comprise light-emitting diodes emitting infrared rays, the localization system being capable of detecting the infrared rays emitted by the diodes to determine the position of the rigid bodies. The localization system may also be of magnetic or ultrasound type.

The computer is connected to the localization system or tridimensional positioning system and is capable of displaying in real time on a display screen the three-dimensional images representative of proximal and distal portions 50 and 52 according to relative positions corresponding to the real relative positions of proximal and distal portions 50 and 52. The surgeon can then follow the displacements of proximal and distal portions 50 and 52 on the display screen. The computer can further display images representative of tools used by the surgeon.

According to an alternative embodiment, to take into account possible motions of the patient on determination of the three-dimensional images, the computer is capable of correcting the positions of the palpation tool or of the ultrasound probe according to the positions of rigid bodies 54, 56.

The surgeon can then displace distal portion 52 of the fractured bone according to the displayed indications to set the fracture, while following in real time the displacement applied to distal portion 52. The computer can regularly determine new values of matrix M", from the position of distal portion 52 provided by the localization system, all along the fracture reduction, and accordingly inform the surgeon.

In subsequent steps of insertion and attachment of the nail by the surgeon, the nail can be equipped with a rigid body having its position determined by the localization system. The computer can display in real time an image representative of the nail, in addition to the images representative of the proximal and distal portions, to assist the surgeon. Further, the positions of the holes of the nail intended to receive the nail attachment screws may be shown. The positions of the holes can be obtained from a model of the nail stored in the computer, or, before insertion of the nail, by means of an adapted palpation tool having its position determined by the localization system. The surgeon uses a drilling tool to drill into the bone openings facing the nail holes. To help the surgeon, the position of the drilling tool is determined and an image representative of the drilling tool, for example, the drilling axis, is shown with the image representative of the nail and of the holes. The surgeon can then easily place the drilling tool with respect to the nail holes before drilling the bone.

According to a variation, the nail is inserted and attached at the level of the proximal portion of the fractured femur before performing the reduction. In this case, the rigid body attached to the bone can be used to determine the position of the proximal portion of the fractured femur. It is then no longer necessary to provide a rigid body directly attached to the proximal portion of the fractured bone.

In the case where the fractured bone corresponds to a single bone including portions that can be considered as symmetrical to each other, for example, a vertebra, it can be considered that the bone comprises two symmetrical portions, a non-fractured portion and a fractured portion, the latter being itself formed of two distinct portions. The method according to the present invention may be identical to what has been previously described with the determination of a three-dimensional image representative of the surface of the non-fractured portion and the determination of two three-dimensional images representative of the surfaces of the two portions of the fractured portion. However, in this case, a portion of the fractured portion is solid with the bone body. It is then possible to determine a singe three-dimensional image which includes both the three-dimensional image representative of the surface of the non-fractured portion and the three-dimensional image representative of the surface of the portion solid with the bone of the fractured portion. Further, the image symmetrical to the three-dimensional image representative of the surface of the non-fractured portion with resect to the plane of symmetry of the bone can be determined. In this case, the obtained symmetrical image directly is in the right position with resect to the portion solid with the bone of the fractured portion. The step of matching the symmetrical image with the three-dimensional image representative of the surface of the portion solid with the bone of the fractured portion can be optionally eliminated, since such a matching is already obtained. It is then sufficient to match the three-dimensional image representative of the portion of the fractured portion which is not solid with the bone with the symmetrical image to determine matrix M".

The present invention has many advantages: first, it enables computer assistance of a surgeon for preparing the reduction of a fracture by indicating to him the gestures to be performed to correctly position one of the portions of the fractured bone with respect to the other; second, it does not irradiate the patient or the surgeon by the implementation of fluoroscopic image forming techniques or by analog techniques, since the present invention can implement ultrasound scanning and/or palpation techniques; third, it decreases surgical complications associated with errors on alignment or positioning of the osseous portions, insertion of the nail, and screwing of the distal screws.

Of course, the present invention is likely to have various alterations and modifications which will occur to those skilled in the art. In particular, in the case where proximal portion 50 must be displaced by the surgeon, the determination of the relative position of the three-dimensional images associated with the proximal and distal portions may be corrected after displacement of the proximal portion and before reduction of the fracture based on the position of proximal portion 50 provided by the localization means. Further, although the use of two-dimensional images obtained by ultrasound scanning has been described for the determination of the three-dimensional images associated with the healthy femur and with the proximal and distal portions of the fractured femur, the images provided by an ultrasound probe (such as those probes sold under the name Voluson from the General Electric Company) capable of directly providing a three-dimensional or volumetric representation of the ultrasound-scanned object may be used for the determination of such three-dimensional images. Moreover, even though the present invention has been described for the reduction of a fracture causing the separation of a bone in bony fragments, the present invention can also be applied to the reduction of several fractures causing the separation of a bone in multiple fragments.

Figure 4A:
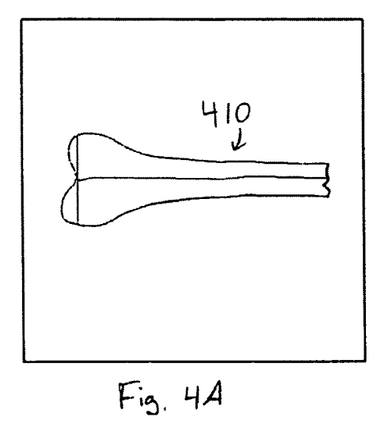
FIG. 4A shows a first bone model.
Figure 4B:
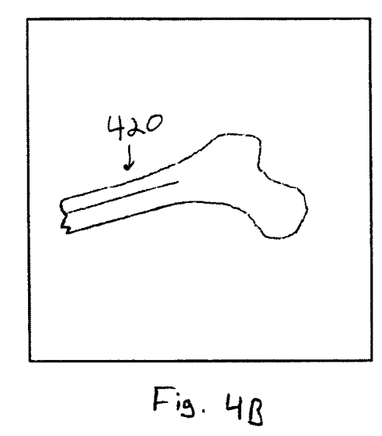
FIG. 4B shows a second bone model.

In one exemplary embodiment, the present invention provides a method for a computer assisted repair of a bone fracture. The method includes the steps of: (a) acquiring intra-operative imaging data of a first bone segment, a second bone segment, and a third bone element; (b) generating a first bone model 410 (FIG. 4A) based upon the imaging data of the first bone segment, and a second bone model 420 (FIG. 4B) based upon the imaging data of the second bone segment, (c) determining an initial position of first and second bone models, (d) generating a third bone model 430 (FIG. 4C) based upon the imaging data of the third bone element, (e) generating a fourth bone model 440 (FIG. 4D) that includes the first and second bone models 410, 420 positioned symmetrically with the third bone model 430, (f) determining a final position of the first and second bone models 410, 420 based upon the fourth bone model 440, and (g) providing position information of the first and second bone models to a user for the reduction of the first and second bone segments. The acquiring step can include the step of acquiring imaging data using an ultrasound probe. The step of generating the first and second bone models can include the steps of determining characteristic points of the first bone segment and the second bone segment and deforming the first and second bone model based upon the determined characteristic points on the first and second bone segments. The position information provided can include translation vectors and rotation angles. The step of determining the third bone model can include the steps of determining characteristic points of the third bone element and generating a third bone model of the third bone element upon the determined characteristic points of the third bone element.

Figure 4C:
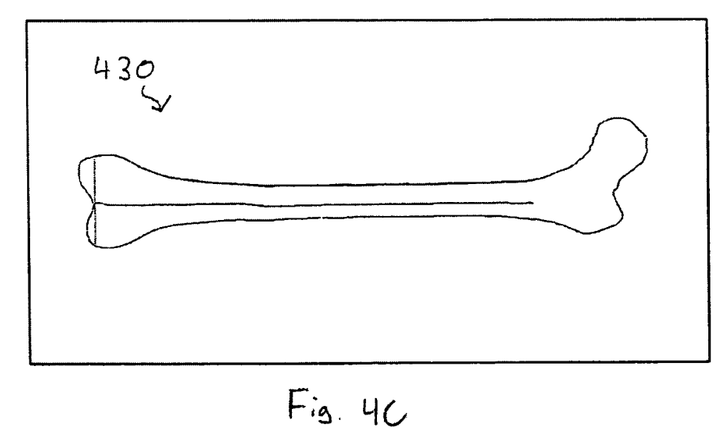
FIG. 4C shows a third bone model.
Figure 4D:
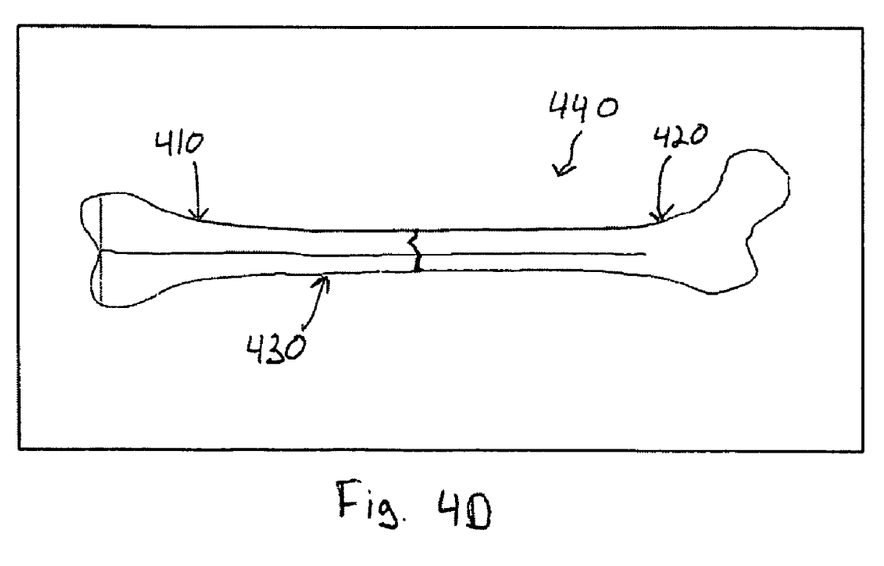
FIG. 4D shows a fourth bone model.

In operation, it is readily understood that in generating the fourth bone model symmetrically with the third bone model, a mirror-image conversion of the third bone model can be generated to facilitate the positioning of the first and second bone models included in the fourth bone model.

In another exemplary embodiment, the present invention provides a method for a computer assisted repair of a bone fracture. The method includes the steps of (a) acquiring intra-operative imaging data of a first bone segment, a second bone segment, and a third bone element; (b) generating a first bone model based upon the imaging data of the first bone segment, and a second bone model based upon the imaging data of the second bone segment, (c) determining an initial position of first and second bone models, (d) generating a third bone model based upon the imaging data of the third bone element, (e) determining a final position of the first and second bone models by positioning the first and second bone models symmetrically with the third bone model, and (f) providing position information of the first and second bone models to a user for the reduction of the first and second bone segments. The acquiring step can include the step of acquiring imaging data using an ultrasound probe. The step of generating the first and second bone models can include the steps of determining characteristic points of the first bone segment and the second bone segment and deforming the first and second bone model based upon the determined characteristic points on the first and second bone segments. The position information provided can include translation vectors and rotation angles. The step of determining the third bone model can include the steps of determining characteristic points of the third bone element and generating a third bone model of the third bone element upon the determined characteristic points of the third bone element.

In another embodiment, the present invention provides for a computer assisted system in support of repairing a bone fracture. The system includes a first locatable element attachable to a first bone segment; a second locatable element attachable to a second bone segment; and a sensor for acquiring intra-operative image data of bone. The system can also include a non-radiation based imaging device, such as a palpation device or an ultrasound probe, for acquiring imaging data of bone. The system further includes a tridimensional positioning system locating the positions of the first and second locatable elements, as well as a computer in communication with the tridimensional positioning system and configured to generate, a first bone model of a bone in response to the sensor acquiring data on the first bone segment; a second bone model of a bone in response to the sensor acquiring data on the second bone segment; a third bone model of a bone in response to the sensor acquiring data on a third bone element; and a fourth bone model, wherein the first and second bone models are repositioned based upon the third bone model. The system also has an interface connected to the computer so as to output the generated first, second, and third bone models. The computer assisted system can further include a bone holder for statically positioning the third bone element having a third locatable element within the tridimensional positioning system. The locatable elements can include a marker which can be in the form of a retro-reflective marker or a light emitting diode. The interface can be display or a screen. The tridimensional positioning system can include infrared emitters and infrared sensors. The computer assisted system can further include a fourth locatable element removably attachable to a nail for connecting the first and second bone segments locatable within the tridimensional positioning system.

In operation, the bone holder having a third locatable element is used to statically position the bone, i.e., the third bone element during the reduction procedure. The advantage of the bone holder is that the third bone model can be generated without having to attach a locatable element to the third bone element.

The embodiments of the present invention are shown and described for purposes of illustration only and not for purposes of limitation. While there have been shown, described, and pointed out fundamental novel features of the invention as applied to several embodiments, it will be understood that various omissions, substitutions, and changes in the form and details of the devices illustrated, and in their operation, may be made by those skilled in the art without departing from the spirit and scope of the invention. Substitutions of elements from one embodiment to another are also fully intended and contemplated. It is also to be understood that the drawings are not necessarily drawn to scale, but that they are merely conceptual in nature. The invention is defined solely with regard to the claims appended hereto, and equivalents of the recitations therein.

The above mentioned patents, applications, and publications are hereby expressly incorporated by reference in their entirety.

What is claimed is:

1. A computer-assisted method for the repair of a bone fracture, comprising the steps of:
   acquiring intra-operative ultrasound imaging data of a first bone segment, a second bone segment, and a third bone element using an ultrasound probe;
   generating, via the computer in communication with the ultrasound probe, a first three-dimensional bone surface model based upon the imaging data of the first bone segment, and a second three-dimensional bone surface model based upon the imaging data of the second bone segment;
   determining an initial position of first and second bone models;
   generating, via the computer, a third bone surface model based upon the imaging data of the third bone element;
   generating, via the computer, a symmetrical mirror image of the third bone model;
   matching the surface of the first bone model to a surface of the mirrored third bone model;
   matching the surface of the second bone model to the surface of the mirrored third bone model;
   determining a final position of the first and second bone models based upon the relative positions of the first bone model and the second bone model after being matched to the mirrored third bone model; and
   providing and displaying on a display connected to the computer position information of the first and second bone models.

2. The method of claim 1, further comprising the steps of: generating a fourth bone model that includes the first and second bone models positioned symmetrically with the third bone model; and determining a final position of the first and second bone models based upon the fourth bone model.

3. The method of claim 1, wherein the step of generating the first and second bone models comprises the steps of: determining characteristic points of the first bone segment and the second bone segment; and deforming the first and second bone model based upon the determined characteristic points of the first and second bone segments.

4. The method of claim 1, wherein the position information comprises translation vectors and rotation angles.

5. The method of claim 1, wherein the step of determining the third bone model comprises the steps of: determining characteristic points of the third bone element; and generating a third bone model of the third bone element based upon the determined characteristic points of the third bone element.

6. A computer assisted system in support of repairing a bone fracture, comprising:
   a first locatable element attachable to a first bone segment;
   a second locatable element attachable to a second bone segment;
   a sensor for acquiring intra-operative ultrasound imaging data of bones;
   a tridimensional positioning system locating the positions of the first and second locatable elements;
   a computer in communication with the tridimensional positioning system and configured to generate:
   a first three-dimensional bone surface model of a bone in response to the sensor acquiring data on the first bone segment;
   a second three-dimensional bone surface model of a bone in response to the sensor acquiring data on the second bone segment;
   a three-dimensional third bone surface model of a bone in response to the sensor acquiring data on a third bone element;
   a symmetrical mirror image of the third bone model; and
   a fourth bone model wherein the first and second bone models are repositioned based upon the third bone model, the computer being configured to match the surface of the first bone model to the surface of the mirrored third bone model and match the surface of the second bone model to the surface of the mirrored third bone model, the computer being configured to determine a final position of the first and second bone models based upon the relative positions of the first bone model and the second bone model after being matched to the mirrored third bone model; and
   an interface connected to the computer so as to output the generated first, second, third, and fourth bone models and position information of the first, second, third, and fourth bone models.

7. The system of claim 6, further comprising a bone holder for statically positioning the third bone element, having a third locatable element locatable within the tridimensional positioning system.

8. The system of claim 6, wherein the locatable element comprises at least one of a retro-reflective marker and a light emitting diode.

9. The system of claim 6, wherein the interface is at least one of a display and a screen.

10. The system of claim 6, wherein the sensor further comprises a palpation device.

11. The system of claim 6, wherein the tridimensional positioning system comprises infrared emitters and infrared sensors.

12. The system of claim 6, further comprising a fourth locatable element removably attachable to a nail for connecting the first and second bone segments locatable within the tridimensional positioning system.

13. A computer assisted system in support of repairing a bone fracture, comprising:
    a first locatable element attachable to a first bone segment;
    a second locatable element attachable to a second bone segment;
    a non-radiation based imaging device for acquiring ultrasound imaging data of bones;
    a tridimensional positioning system locating the positions of the first and second locatable elements; a computer in communication with the tridimensional positioning system and configured to generate:
        a first three-dimensional bone surface model of a bone in response to the sensor acquiring data on the first bone segment;
        a second three-dimensional bone surface model of a bone in response to the sensor acquiring data on the second bone segment;
        a third three-dimensional bone surface model of a bone in response to the sensor acquiring data on a third bone element; and
        a fourth bone model wherein the first and second bone models are repositioned based upon symmetrical mirror image of the third bone model; and
    an interface connected to the computer so as to output the generated first, second, third, and fourth bone models and position information of the first second, third, and fourth bone surface models.

14. The system of claim 13, further comprising a bone holder for statically positioning the third bone element, having a third locatable element locatable within the tridimensional positioning system.

15. The system of claim 13, wherein the locatable element comprises at least one of a retro-reflective marker and a light emitting diode.

16. The system of claim 13, wherein the interface is at least one of a display and a screen.

17. The system of claim 13, wherein the sensor further comprises a palpation device.

18. The system of claim 13, wherein the tridimensional positioning system comprises infrared emitters and infrared sensors.

19. The system of claim 13, further comprising a fourth locatable element removably attachable to a nail for connecting the first and second bone segments locatable within the tridimensional positioning system.

* * * * *